United States Patent [19]

Hunt

[11] Patent Number: 5,623,341
[45] Date of Patent: Apr. 22, 1997

[54] METHOD OF MONITORING A SURFACE USING SURFACE SPECTROSCOPY

[75] Inventor: Jeffrey H. Hunt, Chatsworth, Calif.

[73] Assignee: Rockwell International Corporation, Seal Beach, Calif.

[21] Appl. No.: 200,100

[22] Filed: Feb. 22, 1994

[51] Int. Cl.$^6$ .............................. G01J 3/00; G01N 21/00
[52] U.S. Cl. ........................................ 356/300; 356/237
[58] Field of Search ................................ 356/300, 237; 156/626, 643, 627, 345, 626.1, 643.1, 627.1; 118/712; 427/10

[56] References Cited

U.S. PATENT DOCUMENTS 5,294,289   3/1994   Heinz et al. ........................ 156/626

OTHER PUBLICATIONS

Heinz et al, "Surface Studies with Optical Second Harmonic Generation", Trends in Analytical Chemistry, vol. 8, p. 235t, 1989.
*Studies of Molecular Monolayers at Air–Liquid Interfaces by Second Harmonic Generation: Question of Orientation Phase Transition*, Th. Rasing and Y. R. When, Dept. of Physics, Univ. of California, Berkeley California; M. W. Kim, S. Grubb, and J. Bock, Exxon Research and Engineering Co., Annadale, New Jersey (Springer Ser. Opt. Sci. 1985, vol. 49, Laser Spectros. 7, pp. 307–310).
*Optical Second Harmonic Generation from Langmuir–type Molecular Monolayers*, G. Berkovic Th. Rasing, and Y. R. Shen, Department of Physics, University of California, Center for Advanced Materials, Lawrence Berkeley Laboratory(Proc. SPIE–Int. Soc. Opt. Eng 1988, vol. 824, pp. 115–120.
*Light Waves at the Boundary of Nonlinear Media*, N. Bloembergen and P. S. Pershan, The Physical Review, 128, pp. 193–209, 1962.
*Surface Second Harmonic Generation: A New Technique for Surface Studies*, Y. R. Shen, Ann. Rev. Mater. Sci. 16:69–86, 1986.
*Second–Harmonic Reflection from Silicon Surfaces and Its Relation to Structural Symmetry*, H. W. K. Tom, T. F. Heinz, and Y. R. Shen, Physical Review Letters, pp. 1983–1986, vol. 51, No. 21 21 (Nov. 1983).
*Studies of Surface Enhanced Optical Effects by Second–Harmonic Generation*, Y. R. Shen, Reprinted from Proceedings of the International Conference on Lasers '84, Nov. 26–30, 1984, pp. 234–240.
*Investigation of the Si(111) Surface in UHV: Oxidation and The Effect of Surface Phosphorus*, H. W. K. Tom, X. D. Zhu, Y. R. Shen, and G. A. Somorjai, Reprint from Proceedings of the 17th International Conference on the Physics of Semiconductors, Edited by J. D. Chadi and W. A. Harrison, 1985 by Springer–Verlag New York, Inc.
*Nonlinear Optics and Surface Science*, Y. R. Shen, Mat. Res. Soc. Symp. Proc. vol. 51, pp. 39–49, 1985 Materials Research Society.
*Correlation Between Thermal Desorption Spectroscopy and Optical Second Harmonic Generation For Monitoring Surface Coverages*, Z. D. Zhu and Y. R. Shen, Surface Science 163 (1985) pp. 114–120.

(List continued on next page.)

*Surface Studies By Optical Second Harmonic Generation: An Overview*, Y. R. Shen, J. Vac. Sci. Technol. B3 (5), Sep./Oct. 1985 pp. 1464–1466.

Primary Examiner—K. Hantis
Attorney, Agent, or Firm—Harry B. Field; Steven E. Kahm

[57] ABSTRACT

A method for monitoring a surface is provided. Nonlinear second order surface spectroscopy is used to monitor the condition of a surface. Conditions such as corrosion, contamination and deposition may be monitored. According to the present invention, electromagnetic radiation is directed towards the surface and the second harmonic or other second order frequency responses are monitored to detect the state of the surface. Preferably, a laser, input optics and output optics are utilized to create the second order frequency response that is detected.

19 Claims, 3 Drawing Sheets

OTHER PUBLICATIONS

*Second–harmonic Microscopy of Biological Tissue,* Isaac Freund and Moshe Deutsch, 1986, Optical Society of America, pp. 94–96.

4. *Applications of Optical Second–Harmonic Generation To Surface Science,* Y. R. Shen, Dept. of Physics, University of California, and Materials and Molecular Research Division, Lawrence Berkeley Laboratory, 1986 VCT Publishers, Inc. pp. 151–196.

*Probing the Structure of Freely Suspended Smectic–A Films By Optical Second–Harmonic Generation,* H. Hsiung and Y. R. Shen, 1986, The Americal Physical Society, pp. 4303–4309.

*A Novel Method For Measurements Of Second–Order Non–Linearities Of Organic Molecules,* Th. Rasing, G. Berkovic, Y. R. Shen, vol. 130, No. 1,2, pp. 1–5, Chemical Physics Letters, Sep., 1986.

*A Few Recent Experiments On Surface Studies By Second Harmonic Generation,* Y. R. Shen, pp. 259–266, Plenum Publishing Corporation, 1986.

*Probing Liquid Crystals With Nonlinear Optical Processes,* Y. R. Shen, H. Hsiung, and P. Guyot–Sinnest, Proceedings: Conference on Optics of Liquid Crystals, Naples, Italy, Jul. 15–18, 1986.

*Experiments on Optical Second–Harmonic Generation As A Surface Probe of Electrodes,* G. L. Richmond, H. M. Rojhantalab, J. M. Robinson, and V. L. Shannon, pp. 228–236, J. Opt. Soc. Am. B/vol. 4, No. 2, Feb., 1987.

*Molecular Monolayers and Films,* J. D. Swalen, D. L. Allara, J. D. Andrade, E. A. Chandross, S. Garoff, J. Israelachvili, T. J. McCarthy, R. Murray, R. F. Pease, J. F. Rabolt, K. J. Wynne, and H. Yu, pp. 932–950, Reprinted from Langmuir, 1987.

*Observation of C–H Stretch Vibrations Of Monolayers Of Molecules Optical Sum–Frequency Generation,* J. H. Hunt, P. Guyot–Sionnest and Y. R. Shen, pp. 189–192, vol. 133, No. 3, Chemical Physics Letters, Jan., 1987.

*Second–order Nonlinear Polarizability Of Various Biphenyl Derivatives,* G. Berkovic, Th. Rasing, and Y. R. Shen, pp. 945–949, Reprinted from Journal of the Optical Society of America B, vol. 4, Jun., 1987.

*Local And Nonlocal Surface Nonlinearities For Surface Optical Second Harmonic Generation,* P. Guyot–Sionnest and Y. R. Shen, pp. 1–22, Department of Physics, University of California, May, 1987.

*Optical Second Harmonic Generation as a Probe for Surface Magnetization,* Ru–Pin Pan, Y. R. Shen, pp. 175–178, Chinese Journal of Physics, vol. 25, No. 1, Spring 1987.

*The Effect of Conjugation Length and Electron Donor Groups on the Second Order Nonlinear Polarizability of Cyano Substituted Aromatic Molecules,* G. Berkovic and Y. R. Shen, pp. 607–616, Mol. Cryst. Liq. Cryst., 1987, vol. 150B.

*Polar Ordering of Quasiliquid Crystals—An Optical Second Harmonic Generation Study,* H. Hsiung, Th. Rasing, and Y. R. Shen, pp. 3127–3130, J. Chem. Phys, 87 (5), Sep., 1987.

*Vibration Spectroscopy of a Silane Mololayer at Air/Solid and Liquid/Solid Interfaces Using Sum–Frequency Generation,* P. Guyot–Sionnest, R. Superfine, J. H. Hunt, and Y. R. Shen, pp. 1–18, Center for Advanced Material (LBL–24365 Preprint), Nov., 1987.

*Surface Vibrational Spectroscopy of Molecular Adsorbates on Metals and Semiconductors by Infrared–Visible Sum–Frequency Generation,* R. Superfine, P. Guyot–Sionnest, J. H. Hunt, C. T. Kao, and Y. R. Shen, pp. 1–14, Center for Advanced Materials (LBL–24434 Preprint), Dec., 1987.

*Second Harmonic Generation For In Situ Analysis of Electrode Surface Structure,* Victoria L. Shannon, Daniel A. Koos, and Geraldine L. Richmond, pp. 3579–3583, Applied Optics, vol. 26, No. 17, Sep., 1987.

*Surface Diffusion of CO on Ni(111) Studied by Diffraction of Optical Second–Harmonic Generation off a Monolayer Grating,* X. D. Zhu, Th. Rasing, and Y. R. Shen, pp. 2883–2885, vol. 61, No. 25, Physical Review Letters, Dec., 1988.

*Surface Diffusion Of Carbon Monoxide on Ru(001) Studied Using Laser–Induced Thermal Desorption,* A. A. Deckert, J. L. Brand, M. V. Arena and S. M. George, pp. 441–462, Surface Science 208, 1989, North–Holland, Amsterdam.

*Interaction of Carbon Monoxide With Fe(001),* N. B. Brookes, A. Clarke, and P. D. Johnson, pp. 2764–2767, vol. 63, No. 25, Physical Review Letters, Dec., 1989.

*Nonadiabatic Absorbate Vibrational Damping and Surface Electronic Structure: H on W(001),* Kevin E. Smith and Stephen D. Kevan, pp. 567–570, vol. 64, No. 5, Physical Review Letters, Jan., 1990.

*Ideal Hydrogen Termination of the Si(111) Surface,* G. S. Higashi, Y. J. Chabal, G. W. Trucks, and Krishnan Raghavachari, pp. 656–658, Appl. Phys Lett. 56(7), Feb., 1990.

*Lifetime of an Adsorbate–Substrate Vibration: H on Si(111),* P. Guyot–Sionnest, pp. 2156–2159, vol. 64, No. 18, Physical Review Letters, Apr., 1990.

*Coupling of an Adsorbate Vibration to a Substrate Surface Phonon: H on Si(111),* Y. J. Chabal and G. S. Higashi, pp. 1124–1127, vol. 65, No. 9, Physical Review Letters, Aug., 1990.

*Sensors to Detect the Onset of Localized Corrosion Phenomena,* pp. 1–43, RI/RD92–102P, Proposal for Research Area 2.6, Item 6, Jan., 1992.

*Novel Nondestructive Evaluation (NDE) for Corrosion Detection,* RI/RD92–191P–1, pp. 1–1–6–3, Appendix–1, Technical Proposal, Jan., 1993.

*Research Proposal for Method to Monitor Tribological Surface Chemical Processes,* RI/RD92–110WP, pp. 1–13, Feb., 1992.

METHOD OF MONITORING A SURFACE USING SURFACE SPECTROSCOPY

TABLE OF CONTENTS

ABSTRACT
1. BACKGROUND OF THE INVENTION
   1.1 Some Prior Approaches
   1.2 Historical Development
2. SUMMARY OF THE INVENTION
3. BRIEF DESCRIPTION OF THE DRAWINGS
4. DETAILED DESCRIPTION
   4.1 System Schematic
   4.2 Input Optics
   4.3 Output Optics
   4.4 Illustrative Embodiment
   4.5 Input Light Beam Configuration
   4.6 Calibration
   4.7 Signal Analysis
5 SPECIFIC ILLUSTRATIVE EXAMPLES
   5.1 Corrosion Monitoring
   5.2 Contamination Monitoring
   5.3 Use in LOX-Compatible Environments
   5.4 Material Deposition Monitoring
   5.5 Computer Program for Apparatus Control
6. CONCLUSION
7. CLAIMS

1. BACKGROUND OF THE INVENTION

The present invention relates to monitoring the properties of a surface, specifically, monitoring the surface using electromagnetic radiation. In the most generic sense, surface means the interface between any two media. It can be between gas and a solid, gas and a liquid, between two liquids, between a liquid and a solid, or between two solids, etc.

At an interface between two media one would like to be able, at different times and/or for different applications, to see what the chemical, mechanical, and molecular properties of that interface are. A nonintrusive, nondestructive methods to investigate the interface is desirable. Further, the method should not impose restrictions based on the particular environment around that interface. Because of this, one often uses an electromagnetic radiation technique. Thus, visible light, ultraviolet light, infrared, x-rays, radio frequencies or any other electromagnetic radiation may be used. The frequency at which one or the other interface media is transparent will determine what type (e.g., visible, ultraviolet, etc.) of signal is chosen so that a surface specific response is obtained. For example, linear reflection optical techniques (i.e., the output frequency equals the input frequency), do not provide what is called a surface specific response. Rather, interference from either one or the other media through which the signal must travel or be reflected will result.

1.1 Some Prior Approaches

There are many other techniques which can be used to analyze molecular properties or behavioral properties at an interface. Unfortunately, the vast majority of them have what we characterize as extreme environmental limitations on their application. For example, many of them require that they be applied only in ultra-high high vacuum, which means that anything that a liquid or liquid/solid interfaces may not be tested. In fact, even if one wanted to inspect a vacuum-solid interface, one would have to take ones material to be examined and place it in a high vacuum chamber. This can often be either slow, expensive or impossible depending on the size of the particular material in question.

Other techniques which exist require that the interface be placed in other environments such as at an interface between two solids, in which case it may be necessary,, to destroy the particular material to be studied. Still other techniques require either fabrication of very exotic detection means or require signal integration times which makes them unusable in any sort of real time industrial scenario.

1.2 Historical Development

In nonlinear optics, outputs are produced at sum, difference or harmonic frequencies of the input(s). Using second order nonlinear optical surface spectroscopy to study a surface was originally proposed in the 1960's in "Light Waves at the Boundary of Nonlinear Media" by Bloembergen and P. S. Pershan, The Physical Review, 128, p. 193 (1962). Experimental work involving second harmonic generation was also performed. However, because lasers at the time were comparatively feeble, impractical, slow, etc., there was little subsequent work done on the development of second harmonic generation or, more generally, second order nonlinear optical (NLO) processes at surfaces until considerably later.

More recently, researchers have reviewed NLO processing and concluded that lasers had developed enough that they could be used for studying the physical and chemical properties of surfaces and interfaces. For example, a theoretical study of the physics of the interface and not its engineering aspects has been performed. See Annual Review of Materials Science, "Surface Second Harmonic Generation", Vol. 16, P.69–86 (1986).

However, here we are using NLO techniques to solve pragmatic problems that occur in industry. For example, materials processing, surface contamination, surface corrosion, etc. are problems that are addressed.

2. SUMMARY OF THE INVENTION

A method in accordance with the invention uses a second order nonlinear optical technique to probe an interface between two media. In particular second harmonic generation of a single input or sum-frequency generation of multiple inputs may be utilized.

The fact that a second order process is used means that the reflected signal can only originate at the interface and not by the material the optical probe signal is travelling through nor from the reflected bulk. Thus, the reflected signal is generated from the two or three molecular layers actually at the interface. Because of this, the reflected (output) signal generated is highly surface specific. Consequently, any changes at the interface will result in a very strong change in the intensity of the reflected optic signal.

Frequency generation may include a variety of techniques. For example, if two frequency inputs are used, $f_1$ and $f_2$, the output signal may be $f_1+f_2$ (sum frequency generation) Alternatively the analyzed output signal may be a difference frequency generation of $f_1-f_2$.

3. BRIEF DESCRIPTION OF THE DRAWINGS

4. DETAILED DESCRIPTION

4.1 System Schematic

Figure 1:
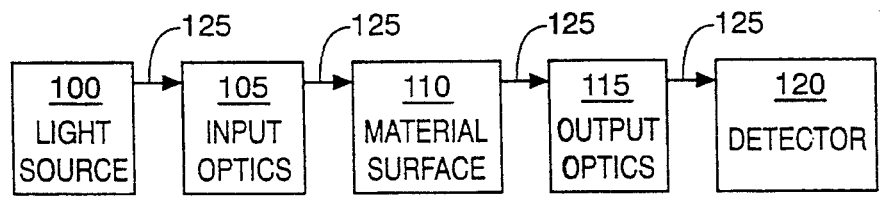
FIG. 1 is a block diagram representation of the system schematic according to the present invention.

FIG. 1 is a block diagram of a surface analysis configuration using a method in accordance with the invention.

Referring to FIG. 1, an input light source is shown at block 100. The light source in block 100 can generate any electromagnetic radiation. However, the input source will typically be a laser. The reason a laser is used is because an optical source of sufficient intensity is needed in order to be able to create a nonlinear optical response at the interface which is probed. What type of laser will vary with the particular application and can range from very large, exotic laser systems, to extremely small lasers; even a simple diode laser may work in some situations.

There is a restriction on the electromagnetic frequency that is the input since one must be able to access the interface with the electromagnetic frequency. That is to say, either one or the other or both media (i.e., those that form the interface) must be transparent to the input and output frequencies because one has to get the input signal to the interface and get the reflected signal away from the interface. Other than this, there are no restrictions on the signal frequencies.

Light source 100 could be a single frequency input. However, in a more general case, it will be two input frequencies which could in fact be fixed frequency inputs or one or both of the frequencies could be tuneable, that is changeable to different frequency inputs depending on the particular application in question.

4.2 Input Optics

Figure 2:
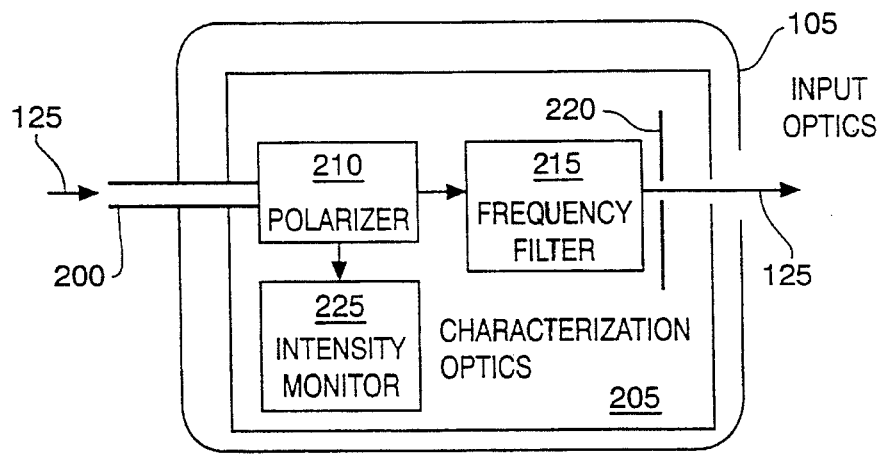
FIG. 2 is a block diagram representation of the input optics shown in FIG. 1.

Input optics 105 functions to move light beam 125 and to characterize the light beam. Referring to FIG. 2, transport optics 200 may be used to position and direct the beam. Transport optics 200 may be, for example, fiber optics or other waveguide mechanisms. Alternatively, transport optics 200 may simply be the air or other medium in which the optical beam is traveling (e.g. a vacuum, a liquid, a transparent solid, etc.).

Input optics 105 also includes characterization optics 205. Characterization optics 205 functions to select a frequency. The one or two input frequencies, are characterized to ensure that only the input frequencies are present and not other frequency components. Other frequency components generated at places other than the surface would mask the signals generated at the surface by the input.

Frequency filter 215 thus filters the light beam to ensure that only the desired frequencies are present. In addition, characterization optics 205 may contain other optional features such as polarizers 210, iris or spatial filters 220 and intensity monitors 225.

Additionally, although we have separated transport and characterization optics, a system could be designed so that both transport and characterization tasks could be done in a single, specifically designed entity. One example might be a polarization preserving optical fiber which would automatically take care of polarization characteristics. Further, the input fiber might in fact be given frequency selective properties so that in addition to transporting the light, the necessary frequency selection could be performed.

There are a large number of devices that perform frequency selection. One of simplest and cheapest of these is a color filter. This is an object that, for instance, will pass only frequencies lower than the input frequency and will generally be opaque to frequencies at harmonics or other higher frequencies. One example of a frequency selective device with better optical properties than a color filter is a holographically designed filter. Other examples include a monochromator or diffraction grading. Virtually any frequency selective or frequency dependent entity could be used as long as the input light is in fact filtered to be composed of only the frequencies which are desired.

4.3 Output Optics

Output optics 115 serves the purpose of transporting the output signal to the detection device and performing the appropriate frequency selection to make sure that the signal which is being detected is in fact the signal that is produced at the interface rather than a spurious signal generated elsewhere (such as the optical components).

Output optics 115 may be largely the same as input optics 105. The difference primarily is that in the input optics one is trying to make sure that the light going to the surface is only the input frequencies. After leaving the surface one wants to make sure that the frequency selection device only allows the transmittal of the second order signal at the output frequency reflected from the interface, such as a second harmonic frequency, sum frequency or the difference frequency. To accomplish this, frequency selective optic (e.g., color filters, etc.) be used.

Frequency selection accomplishes two tasks: (1) it makes sure that the detection system sees only the output (reflected) signal desired, and (2) it immediately removes the input frequencies or input fundamentals so that additional frequencies are not produced by the inputs traveling through the subsequent optical components.

As with the input optics, the output optics may optionally include a polarizer and spatial filter. Since the polarization of the output signal may or may not be the same as the polarization of the input signal, the output polarization selective device may or may not be of the same orientation at the input polarization selection device. This will depend upon the particular sample and the particular configuration being used.

4.4 Illustrative Embodiment

Figure 3:
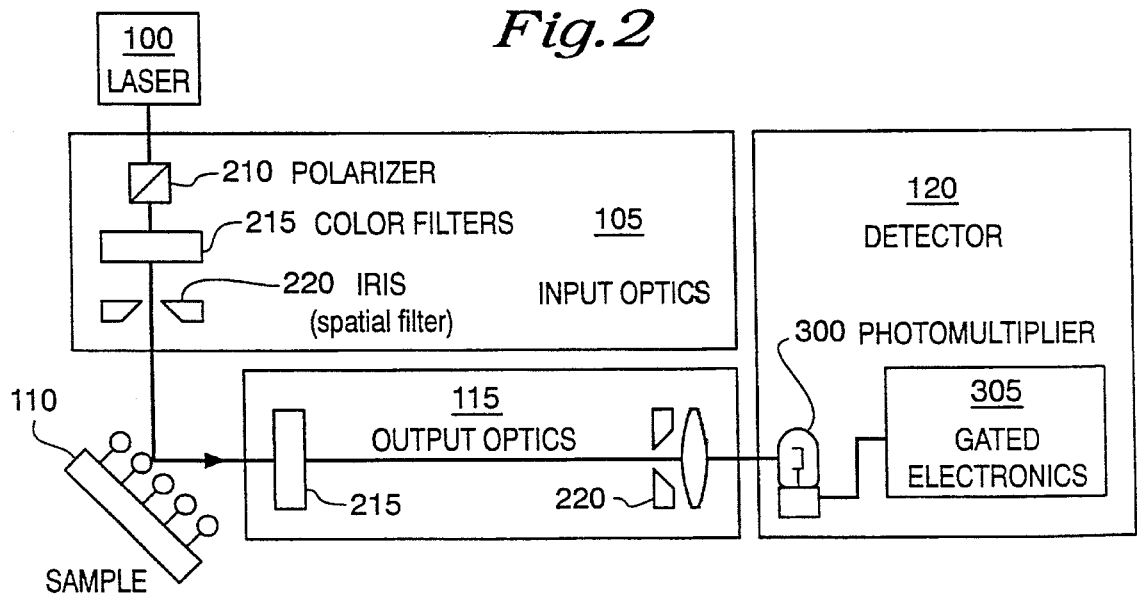
FIG. 3 is a more detailed block diagram representation of the system schematic shown in FIG. 1.

FIG. 3 shows one physical embodiment of the system described in FIG. 1. Laser 100 generates a laser beam which travels through input optics 105 to strike sample 110. The reflected beam travels through output optics 115 and it is then detected at detector 120. Input optics 105 includes various components and options as discussed with reference to FIG. 2. Output optics 115 also includes filter 215 and iris 220. Detector 120 may include photomultiplier 300 and electronics 305.

The signal generated at the interface will typically be of a relatively low light level, perhaps in the one to a few thousand photon level. Consequently one can not use an arbitrary, detector, and, in fact, needs a detector for low light level detection such as a photomultiplier. One can also use avalanche photodiodes, which are solid-state analogs of photomultipliers. However, even though these are low light level detectors, they are off the shelf devices and do not require any additional engineering other than connection to typical gated integration electronics, etc., in order to be able to measure the electronic response of the detectors after the input radiation is detected.

As shown in FIG. 3, the output signal is reflected off the front of sample 110. However, other configurations are possible. For example, if sample 110 is also transparent (i.e. both media that form the interface are transparent), the output signal may pass through sample 110 and exit the rear of sample 110. Thus in this case, output optics 15 and detector 120 may be located behind sample 110.

4.5 Input Light Beam Configuration

Figure 4:
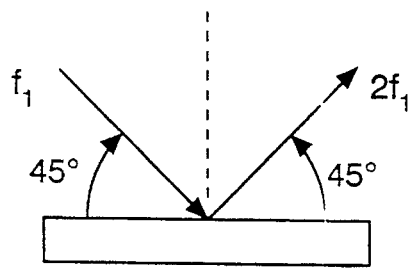
FIGS. 4, 4A and 4B are diagrams of various input light beam configurations that may be used according to the present invention.

Referring to FIG. 4, several possible angles of incidence for a light beam or beams are shown. The input beam shown in the simplest configuration has a single input which is incident at 45° with a subsequent reflected second harmonic output also at 45°. This is one very particular case of the technique.

Figure 4A:
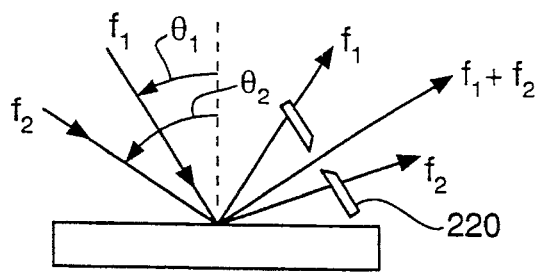

FIG. 4A illustrates a more general case where there are two beams of frequencies $f_1$ and $f_2$ input at different angles of incidence $\Theta_1$ and $\Theta_2$. In the case where the input beams are at different angles, the reflected beams will be also at different angles and the generated signal such as $f_1+f_2$ will be at another angle different from the $f_1$ and $f_2$ output specular reflections. If, of course, the two input beams are made to be co-linear, then the specular reflections will also be co-linear and the output signal will be co-linear with the two specular reflected beams. This is, however, not the general case.

Figure 4B:
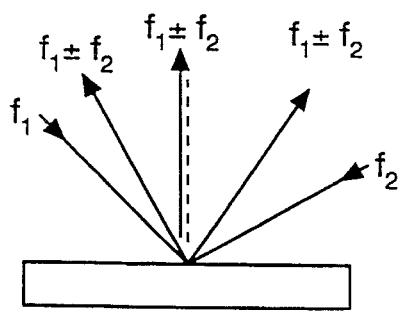

The two beams do not have to be input from the same side. As shown in FIG. 4B, the inputs can, in fact, come from differing sides of the sample and hit the same spot, which will then mean that the output beam could, in fact, be generated directly away from the surface or possibly at some angle, depending upon the input frequencies $f_1$ and $f_2$ and depending upon the specific optical properties of the interface.

There is one caveat to the preceding generalization however. The input signal beams can not be normal to the surface. One can show that if the inputs are normal to the surface it will not be possible to produce any output signal.

When the two input beams are not co-linear, their reflections will not be colinear and therefore, the output signal will be at an angle which is different from the two specular reflections. Consequently, in this case the first element in the output optics may be an iris, for the simple reason that since the output signal will be at a different angle from the two specular reflections, the iris can be positioned in a way that it blocks the specular reflections of the fundamentals, while transmitting the output signal. Thus, as shown in FIG. 4A, iris 220 may be used to pass the $f_1+f_2$ reflection while blocking the remaining reflections. So in this sense, even though this is merely a spatial filter, it is, in fact, doing a first order frequency selection.

4.6 Calibration

In general, when one is setting up an experimental apparatus to do nonlinear optical surface monitoring, there will be a frequency response in the detector input optics, the output optics, and even the laser itself, which are not to be looked at, in addition to the properties on the surface (e.g., surface roughness). Since each of these optics may have a frequency or intensity dependence which is not to be monitored, an external reference/calibration system is needed for use with the regular optical experimentation set up.

The reference optics typically will incorporate some optical entity which has a small nonlinear optical response. For example, one could use in transmission a piece of quartz, or in reflection some semiconductor such as Gallium Arsenide with a strong bulk nonlinear optical response. This reference could in one case be temporarily placed directly in the beam path, consequently having the signal measured with the same detection system which is measuring the surface reflection. In this case, the large signal generated by the reference optic will completely overwhelm the signal from the sample surface and just measure the large reference response. Then, a comparison between the surface signal strength and the reference sample strength is made. From this, one can remove undesired optical changes and make sure that the changes in the signal are being measured are due only to the changes occurring at the surface. Alternatively, one could divert part of the input beam or beams to a simulated surface off to the side of the main experimental set-up which can then produce a large signal either in reflection or transmission, and have that large signal sent off to a detection system. In this way, simultaneous reference generation can be obtained at the same time as making a measurement of the service properties via the nonlinear optical technique.

4.7 Signal Analysis

Figure 5:
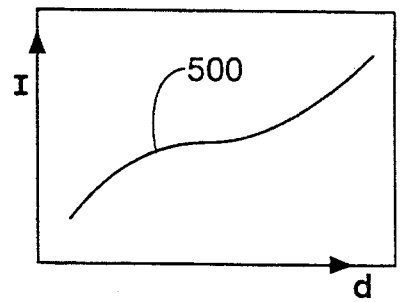
FIG. 5 is a graph of a detected signal intensity that varies with sample positions.

Signal intensity at detector 120 may be measured as a function of a variety of variables. With reference to FIG. 5, the intensity (I), of detected signal 500 is shown to vary with the sample position (d).

The graph shows the intensity of the detected signal as a function of position on a given surface or interface. In this case, differing chemical or physical characteristics of the surface result in a change in the intensity of the detected signal as different locations of the surface are analyzed. This change in the amount of signal strength indicates that there are different chemical or physical properties of the interface at the different positions of the surface.

Figure 5A:
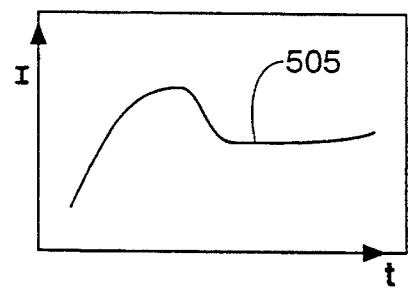
FIG. 5A is a graph of a detected signal intensity that varies over time.

FIG. 5A illustrates the intensity (I) of a detected signal varying with respect to time (t). In signal 505 a certain interface parameter (e.g., a chemical or physical property) has been changed or is intentionally being changed as a function of time. As the specific properties of the interface vary with time, the intensity of the detected signal will vary as time. This is shown in FIG. 5A as a time varying plot of intensity.

Figure 5B:
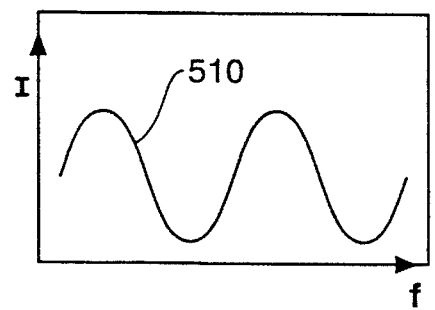
FIG. 5B is a graph of a detected signal intensity that varies with frequencies.

FIG. 5B illustrates yet another example of the intensity of the detected signal changing. In this case, the intensity of detected signal 510 varies as a function of frequency (f). It specifically varies as a function of the input frequency similar to classical linear absorption spectroscopy where the intensity of light is measured in transmission through material. Here, we are looking at the intensity (I) of the output signal as a function of the frequency (f) of the input signal. As different chemical processes occur at the interface, they will lead to a modification of the spectral response of the interface. This leads to a modification of the spectral intensity of the output signal as a function of the input signal's frequency.

In a preferred method, the input frequency may be changed by using two input lasers. Preferably, one laser has a fixed frequency, the second laser has a tunable frequency, and the detected signal is the sum frequency of the two laser frequencies used. In a still more preferred method, the fixed frequency is in the visible range and the tunable frequency is in the infrared range. Thus, the frequency of the detected signal is a function of the tunable frequency and a spectrum of output signals may be detected as the tunable frequency is changed.

In addition to intensity and spectral changes, there can at times be a desire to measure polarization dependence of the input and output signals as a function of whatever surface characteristics are being changed. Specifically, through the nature of the nonlinear optical process at the interface, for a given input polarization only certain output polarization combinations can be produced. Violation of these polarization combinations can lead one to determine what specific mechanical, physical, or molecular orientation properties are occurring on the surface as a given characteristic of the surface is being modified.

5. SPECIFIC ILLUSTRATIVE EXAMPLES

5.1 Corrosion Monitoring

Figure 6:
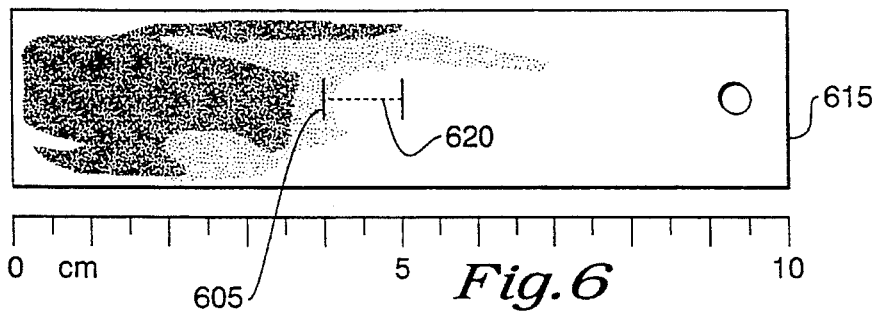
FIG. 6 shows a piece of copper having corrosion on its surface.
Figure 6A:
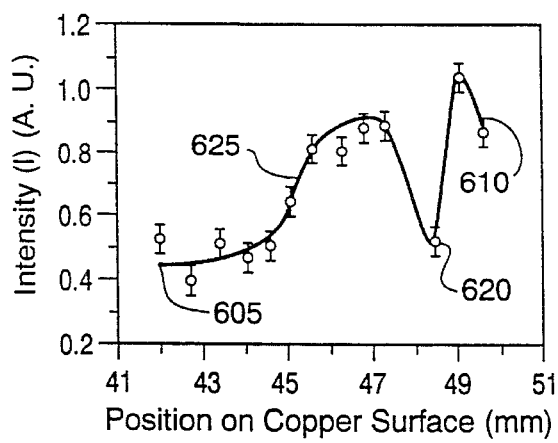
FIG. 6A is a graph showing the detected signal intensity versus position of the copper piece of FIG. 6.

FIG. 6 illustrates a copper coupon (simply a polished piece of copper). Copper coupon 600 has been rusted as shown by shading 615. In this example, intensity will be measured as a function of the change across the copper coupon 600. Thus, a change of intensity will be shown between position 605 on copper coupon 600 and position 610 on copper coupon 600. FIG. 6A illustrates the change in intensity of signal 625 from position 605 to position 610.

As can be seen, a second harmonic signal at position 605 is reduced to approximately a factor of two relative to that at 610. Consequently, the corroded portion of the copper at 605 has a much smaller signal than at 610, and as a result, shows that the second harmonic is useful for detecting when surface corrosion has occurred. Notice specifically at position 620 a strong dip in the level of the detected signal. If one examines the surface of copper coupon 600, position 620 corresponds to a small blemish present in the otherwise clean area of the copper. Thus, nonlinear second order surface spectroscopy may be used to detect the presence of corrosion on a copper sample.

5.2 Contamination Monitoring

Figure 7:
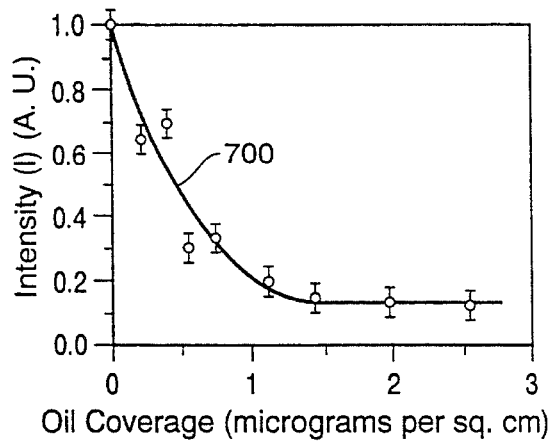
FIG. 7 is a graph illustrating the change in detected signal intensity versus contamination.

The detected signal can also represent the level of contamination on a surface. This level of contamination may change over time and may be monitored. For example, FIG. 7 shows the second harmonic signal 700 from a clean metal coupon as a function of oil coverage on the surface. In this example, the oil coverage is created by dousing the surface with a small amount of freon which has been contaminated with a commercial industrial lubricant (either Way-Lube or Vactra machining oil). After the contaminated freon is deposited on the surface the freon evaporates leaving an oil residue on the surface. After each measured deposition of contaminated freon onto the surface, the second harmonic signal 700 is measured, and a subsequent graph is made of the intensity (I) of the second harmonic signal as a function of the oil coverage, in this case measured in micrograms per square centimeter. As can be seen from FIG. 7, signal 700 drops by a factor of 5 from a clean metal coupon to the case where 1 to 2 micrograms per square centimeter is present on the surface.

In both prior examples, the particular input laser used was a mode-locked continuous wave Nd:YAG laser with an output at 1.064 micron. The output comes in a series of pulse envelopes. The envelopes are produced at 10 Hz. Each envelope contains 100 pulses separated by 10 ns (nanosecond). Each individual pulse is 100 ps (picosecond) in duration. The envelopes are amplified to sufficient energies so that they can produce signal above the detector noise level. The system output was doubled so that its output wavelength was 532 nanometers or 0.532 micron. The 0.532 micron signal then served as the input frequency onto the surface. Since a second harmonic generation frequency outputs were detected, experiment, the output detected was that of a second harmonic of the 532 nanometers signal, a wavelength of 266 nanometers.

5.3 Use in LOX-Compatible Environments

An advantage of the method described above is that surface corrosion or contamination (together simply called contamination) of structures such as LOX- (liquid oxygen) compatible engine components can be detected in a noninvasive, nondestructive fashion. The method is sensitive enough to detect very low levels of surface contamination; to levels compatible with engine parts that must operate in a LOX environment. (For example, a standard NASA specification for LOX-compatible hardware is that surface contamination of the hardware cannot exceed 1 milligram per square foot, which translates to approximately 1 microgram per square centimeter.)

5.4 Material Deposition Monitoring

Figure 8:
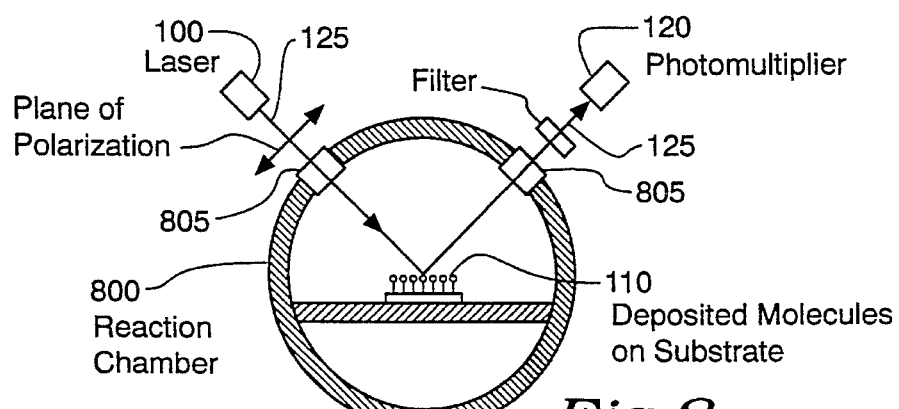
FIG. 8 illustrates a system according to the present invention to monitor the deposition of material upon a substrate.

FIG. 8 illustrates the use of the present invention to monitor the thickness of a material deposited on sample 110. Laser 100 is directed towards a reaction chamber 800 in which a material is being deposited on sample 110. For example, reaction chamber 800 may be used to deposit a thin film on a semiconductor substrate or deposit a semiconductor on a substrate. The reflected beam is then monitored through detector 120. Though not shown in FIG. 8, it would be understood by one of ordinary skill that other associated optics may also be present similar to FIG. 3. Reaction chamber 800 has optical ports 805, through which the output or reflected beam may travel.

Although we have illustrated a case where the laser input, detection optics, and detection apparatus are outside of the reaction chamber, the laser could be made smaller and placed directly inside the chamber, as well as having the subsequent detection optics and photomultiplier inside the chamber as well.

Typically, one would measure the response of the detected signal as a function of the amount of material deposited onto the substrate in question. One would expect a substrate absent of deposited material to have a certain second harmonic intensity level. When a semiconductor, for example, is deposited on the substrate, this level would more than likely increase as single monolayer is deposited. As the coverage increases to levels greater than one monolayer, the smooth layer will begin to form islands of material. This will result in a local field enhancement of the input laser beam at the surface, resulting in an increase in the second harmonic signal detected. As material continues to be deposited on the surface, the islands will begin to subside and form a smoother molecular coating. This will lead to a decrease in the local field enhancement and consequently, one will see a reduction in the second harmonic intensity level. An intensity versus time signal such as signal 505 in FIG. 5A may, therefore, result. Thus, nonlinear second order surface spectroscopy may be used to provide an in-situ method of determining the mechanical and electrical properties of a material during deposition.

5.5 Computer Program for Apparatus Control

The apparatus shown in the figures may be controlled by a suitably programmed computer device having a program storage device in which a program of machine-readable instructions for performing the techniques is encoded. For example, the apparatus may be controlled by a hand-held computer having a read-only memory (ROM) encoding machine-executable instructions for performing some or all of the techniques described above. Alternatively, the program storage device may comprise, e.g., a floppy disk, a CD-ROM, etc.; the machine-readable instructions may comprise source code (compilable or interpretable). Creation of a program of instructions suitable for the desired application is a matter of routine for those of ordinary skill having the benefit of this disclosure.

6. CONCLUSION

It will be apparent to those of ordinary skill having the benefit of this disclosure that the techniques described above represent a novel adaptation of known surface chemistry techniques, previously used in academic research settings, to solve significant industrial problems that, with hindsight, are seen as analogous to the prior work. The adaptation permits quick, cost-effective characterization of a surface or interface of which the chemical physical properties are unknown and which to be analyzed.

No claim is made to the use of nonlinear second harmonic generation and frequency generation surface spectroscopy. Rather, the claims are directed to the industrial-type subject matter set forth herein. It will, however, be appreciated by those of ordinary skill having the benefit of this disclosure that numerous variations from the foregoing illustration will be possible without departing from the inventive concept described herein. Accordingly, it is the claims set forth below, and not merely the foregoing illustrations, which are intended to define the rights claimed.

What is claimed is:

1. A method of detecting a surface contamination of an engine component, comprising:
   (a) directing at least two laser beams to an area of the engine component, wherein each of said at least two laser beam is directed through an input filter which attenuates frequencies higher than a fundamental frequency of a specified one of said at least two laser beams;
   (b) passing a respective reflection of each of said at least two laser beams from said engine component through an output filter which attenuates frequencies lower than a sum frequency of said at least two laser beams; and
   (c) monitoring the intensity of said sum frequency.

2. The method of claim 1, wherein one of said laser beams is at a fixed visible frequency and one of said laser beams is at a tunable infrared frequency.

3. A method of in situ monitoring of corrosion of a surface of a machinery component at an interface between said surface and an adjacent medium, comprising:
   (a) directing electromagnetic radiation, referred to as directed radiation, to an area of the interface; and
   b) monitoring a parameter of electromagnetic radiation, referred to as second-order radiation, generated by a second-order radiation response of the interface to the directed radiation, said parameter being referred to as a second-order parameter, wherein said second-order parameter varies with said corrosion.

4. The method of claim 3, wherein the second-order radiation response is a reflection of the directed radiation from the interface.

5. The method of claim 4, wherein said second-order parameter comprises an intensity parameter of said reflection.

6. The method of claim 3, wherein said corrision varies as a function of time.

7. The method of claim 3, wherein said corrision varies as a function of the location of said area of the interface.

8. The method of claim 3, wherein said second-order parameter varies as a function of the frequency of said directed radiation.

9. The method of claim 3, wherein said directing step comprises directing electromagnetic radiation from a single source of radiation.

10. The method of claim 9, wherein said second order radiation has a frequency that is a second harmonic of said single source of radiation.

11. The method of claim 3, wherein said directing step comprises directing electromagnetic radiation from a plurality of sources of radiation.

12. The method of claim 11, wherein a first one of said plurality of sources of radiation emits radiation at a frequency different from that of a second one of said plurality of sources of radiation.

13. A method of detecting a surface contamination of an engine component, comprising:
   (a) directing electromagnetic radiation, referred to as directed radiation, to an area of the engine component; and
   (b) monitoring an intensity parameter of electromagnetic radiation, referred to as second-order radiation, generated by reflection of said directed radiation from the engine component, wherein said intensity parameter changes in the presence of said surface contamination.

14. The method of claim 13, wherein said surface contamination comprises rust.

15. The method of claim 13, wherein said surface contamination comprises oil.

16. A method of detecting a surface contamination of an engine component, comprising:

(a) directing at least one laser beam to an area of the engine component, wherein each of said at least one laser beam is directed through an input filter which attenuates frequencies higher than a fundamental frequency of a specified one of said at least one laser beam;

(b) passing a respective reflection of each of said at least one laser beam from said engine component through an output filter which attenuates frequencies lower than a specified frequency; and (c) monitoring the intensity of said specified frequency, said specified frequency being a second order frequency.

17. The method of claim 16, wherein said specified frequency is a second harmonic of said fundamental frequency.

18. The method of claim 16, wherein (a) said directing of at least one laser beam comprises directing at least two laser beams, and (b) said specified frequency is a sum frequency or a difference frequency of two of said at least two laser beams.

19. A program storage device readable by a machine and encoding a program of instructions for performing the method steps of a specified one of claims 1 through 18.

* * * * *